US00PP17616P2

(12) United States Plant Patent

Murakami

(10) Patent No.: US PP17,616 P2

(45) Date of Patent: Apr. 17, 2007

(54) *CALIBRACHOA* PLANT NAMED 'SUNBELRICHIPI'

(50) Latin Name: ***Calibrachoa* sp.**
Varietal Denomination: Sunbelrichipi

(75) Inventor: Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/259,236

(22) Filed: Oct. 26, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Calibrachoa* plant named 'Sunbelrichipi', characterized by its upright and outwardly spreading plant habit; vigorous growth habit; freely branching habit; freely flowering habit; long flowering period; red purple-colored flowers; and good weather tolerance.

1 Drawing Sheet

Botanical designation: *Calibrachoa* sp.
Cultivar denomination: 'Sunbelrichipi'.

BACKGROUND OF THE INVENTION

The present Invention relates to a new and distinct cultivar of *Calibrachoa* plant, botanically known as *Calibrachoa* sp., and hereinafter referred to by the cultivar name 'Sunbelrichipi'.

The new *Calibrachoa* is a product of a planned breeding program conducted by the Inventor in Higashiomi, Shiga, Japan. The objective of the breeding program is to create new outwardly spreading *Calibrachoas* with large and attractive flowers.

The new *Calibrachoa* originated from a cross-pollination made by the Inventor in July, 1995, of a proprietary selection of *Calibrachoa cornuta* identified as code number CH4, not patented, as the female, or seed, parent with a proprietary selection of *Calibrachoa cornuta* identified as code number PR5, not patented, as the male, or pollen, parent. The new *Calibrachoa* was selected as a single plant from the resulting progeny of the cross-pollination by the Inventor in a controlled environment in Higashiomi, Shiga, Japan.

Asexual reproduction of the new cultivar by terminal cuttings in a controlled environment in Higashiomi, Shiga, Japan since October, 1998, has shown that the unique features of this new *Calibrachoa* are stable and reproduced true to type in successive generations.

SUMMARY OF THE INVENTION

Plants of the cultivar Sunbelrichipi have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Sunbelrichipi'. These characteristics in combination distinguish 'Sunbelrichipi' as a new and distinct cultivar of *Calibrachoa:*

1. Upright and outwardly spreading plant habit.
2. Vigorous growth habit.
3. Freely branching habit.
4. Freely flowering habit.
5. Long flowering period.
6. Red purple-colored flowers.
7. Good weather tolerance; tolerant to rain and low and high temperatures.

Plants of the new *Calibrachoa* differ from plants of the female parent selection in plant and flower size as plants of the new *Calibrachoa* are taller and have larger flowers than plants of the female parent selection. Plants of the new *Calibrachoa* differ primarily from plants of the male parent selection in flower color as plants of the male parent selection have purple-colored flowers.

Plants of the new *Calibrachoa* can be compared to plants of the cultivar Sunbelochipi, disclosed in U.S. Plant Pat. No. 10,355. In side-by-side comparisons conducted in Higashiomi, Shiga, Japan, plants of the new *Calibrachoa* were taller and narrower plants of the cultivar Sunbelochipi. In addition, plants of the new *Calibrachoa* had larger flowers than plants of the cultivar Sunbelochipi.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of a typical flowering plant of 'Sunbelrichipi' grown in a container.

The photograph at the bottom of the sheet is a close-up view of typical flowers and leaves of 'Sunbelrichipi'.

DETAILED BOTANICAL DESCRIPTION

In the following description, color references are made to The Royal Horticultural Society Colour Chart, 2001 Edition, except where general terms of ordinary dictionary significance are used. Plants grown in 25-cm containers for about four months were used for the aforementioned photographs and following description. Plants were grown under conditions which closely approximate commercial production conditions during the early spring in Higashiomi, Shiga, Japan in a polyethylene-covered greenhouse. During the production period, day temperatures were about 18° C. and night temperatures were about 15.5° C. Plants were pinched one time in the spring.

Botanical classification: *Calibrachoa* sp. cultivar Sunbelrichipi.

Parentage:

*Female, or seed, parent.*—Proprietary selection of *Calibrachoa* sp. identified as code number CH4, not patented.

*Male, or pollen, parent.*—Proprietary selection of *Calibrachoa* sp. identified as code number PR5, not patented.

Propagation:

*Type cutting.*—Terminal vegetative cuttings.

*Time to initiate roots.*—About one week at 20° C. to 25° C.

*Time to produce a your rooted plant.*—About three weeks at 20° C. to 25° C.

*Root description.*—Fine, fibrous, fleshy; light brown in color.

*Rooting habit.*—Freely branching.

Plant description:

*Plant form and growth habit.*—Annual flowering plant; upright and outwardly spreading plant habit. Vigorous growth habit.

*Plant height.*—About 23 cm.

*Plant diameter.*—About 46.8 cm.

*Branching habit.*—Freely branching, about 30 lateral branches potentially develop per plant; pinching enhances lateral branch development.

*Lateral branch description.*—Length: About 26.8 cm. Diameter: About 2.7 mm. Internode length: About 1 cm. Texture: Pubescent. Color: 187A.

*Foliage description.*—Arrangement: Alternate; simple. Length: About 4 cm. Width: About 1.3 cm. Shape: Narrowly elliptic. Apex: Obtuse. Base: Cuneate. Margin: Entire. Texture, upper and lower surfaces: Pubescent. Venation pattern: Pinnate; reticulate. Color: Developing and fully expanded foliage, upper surface: 144A; venation, close to 144D. Developing and fully expanded foliage, lower surface: 144B; venation, close to 144D. Petiole length: About 1 mm. Petiole diameter: About 0.6 mm. Petiole texture, upper and lower surfaces: Pubescent. Petiole color, upper and lower surfaces: 144D.

Flower description:

*Flower type and habit.*—Flowers face upright or outward; single, axillary; salverform. Flowers not persistent. Freely flowering habit, numerous flowers per plant, about two flowers develop per lateral branch. Flowers not fragrant.

*Natural flowering season.*—Spring to late autumn in Japan; flowering continuous during this period.

*Time to flower.*—Early flowering; plants begin flowering about two to three weeks after planting.

*Flower longevity on the plane.*—About seven to ten days.

*Flower size.*—Diameter: About 3.9 cm. Depth: About 2.7 cm. Throat diameter (distal): About 6.3 mm. Tube diameter (proximal): About 2.1 mm.

*Flower buds.*—Length: About 2.5 cm. Diameter: About 5.5 cm. Shape: Elongated oblong. Color: 64B; longitudinal lines, 147A.

*Corolla.*—Arrangement/appearance: Single whorl of five petals fused into flared trumpet. Petal length from throat: About 1.7 cm. Petal width: About 1.7 cm. Petal shape: Spatulate. Petal apex: Rounded. Petal margin: Entire. Petal texture, upper and lower surfaces: Smooth, glabrous; satiny. Color: Petal, when opening and fully opened, upper surface: N57B; venation, N57B. Petal, when opening and fully opened, lower surface: N66B; venation, N187A. Flower throat (inside): 9A. Flower tube (outside): 154C; longitudinal lines, N187A.

*Sepals.*—Arrangement/appearance: Single whorl of five sepals fused at base; star-shaped calyx. Length: About 1.5 cm. Width: About 2.7 mm. Shape: Lanceolate. Apex: Acute. Margin: Entire. Texture, upper and lower surfaces: Pubescent. Color, upper surface: 145A. Color, lower surface: 145A; longitudinal lines, 147A.

*Peduncles.*—Length: About 1.9 cm. Width: About 0.7 mm. Strength: Moderately strong. Texture: Smooth, glabrous. Color: 187A.

*Reproductive organs.*—Stamens: Quantity: Five per flower. Anther shape: Ellipsoidal. Anther length: About 1 mm. Anther color: 13C. Pollen amount: Moderate. Pollen color: 9C. Pistils: Quantity: One per flower. Pistil length: About 1.1 cm. Stigma shape: Ellipsoidal. Stigma color: 144A. Style length: About 8.2 mm. Style color: 144C. Ovary color: 144B.

*Seeds.*—Seed development has not been observed.

Disease/pest resistance: Plants of the new *Calibrachoa* have not been noted to be resistant to pathogens and pests common to *Calibrachoas.*

Weather/temperature tolerance: Plants of the new *Calibrachoa* are tolerant to rain and wind and have been observed to tolerate temperatures from 0° C. to 35° C.

It is claimed:

1. A new and distinct cultivar of *Calibrachoa* plant named 'Sunbelrichipi', as illustrated and described.

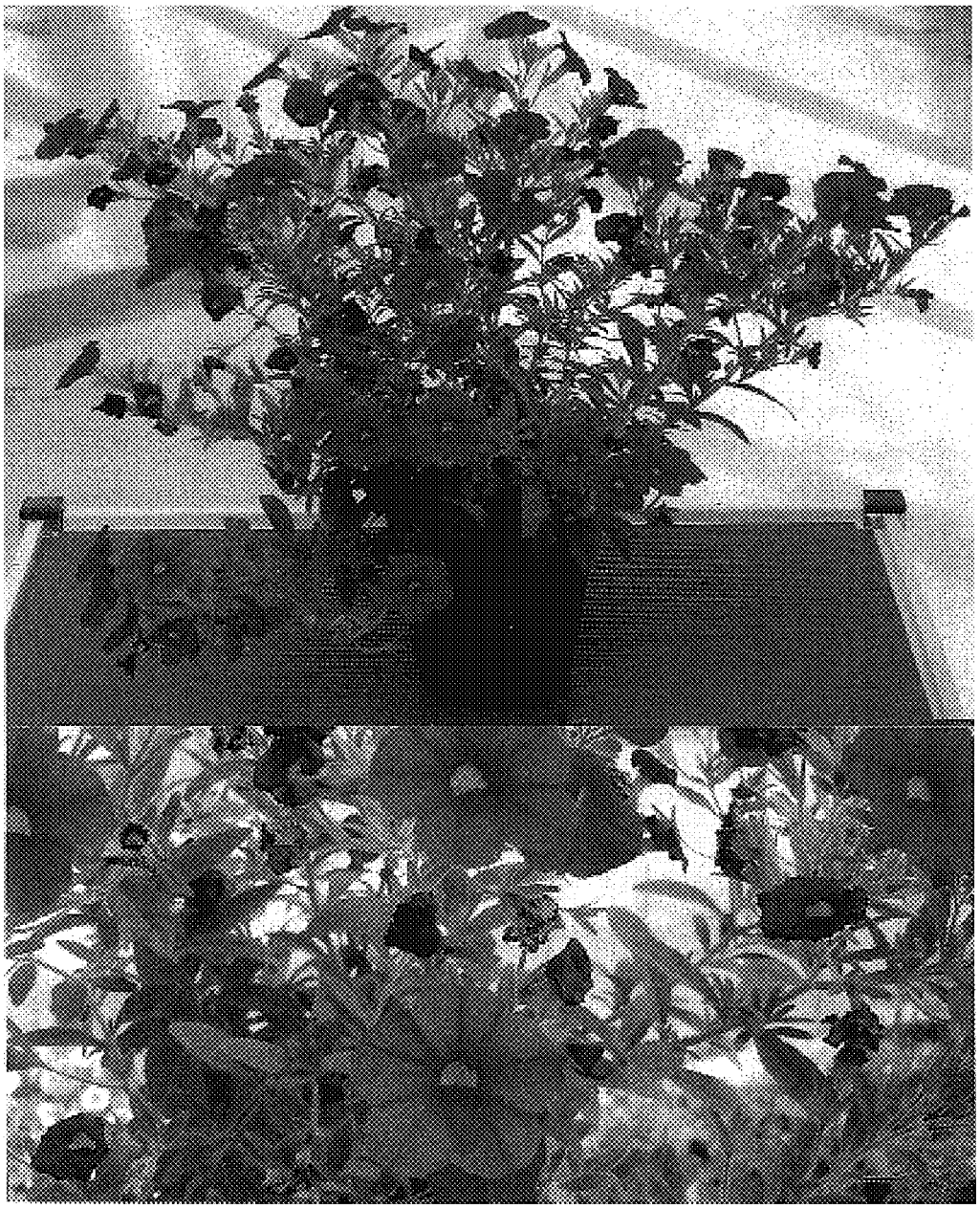

* * * * *